(12) United States Patent
Mayo et al.

(10) Patent No.: US 8,952,094 B2
(45) Date of Patent: Feb. 10, 2015

(54) REVERSIBLE POLYMER COMPOSITION

(71) Applicant: Xerox Corporation, Norwalk, CT (US)

(72) Inventors: James D. Mayo, Mississauga (CA); Stephan Drappel, Toronto (CA); C. Geoffrey Allen, Waterdown (CA); Biby E. Abraham, Mississauga (CA); Sonja Hadzidedic, Oakville (CA)

(73) Assignee: Xerox Corporation, Norwalk, CT (US)

( * ) Notice: Subject to any disclaimer, the term of this patent is extended or adjusted under 35 U.S.C. 154(b) by 84 days.

(21) Appl. No.: 13/905,314

(22) Filed: May 30, 2013

(65) Prior Publication Data

US 2014/0357783 A1 Dec. 4, 2014

(51) Int. Cl.
C07D 307/38 (2006.01)
C09D 11/30 (2014.01)

(52) U.S. Cl.
CPC .............. *C09D 11/30* (2013.01); *C07D 307/38* (2013.01)
USPC ............................. 524/879; 549/472; 549/491

(58) Field of Classification Search
CPC ............................. C09D 11/30; C07D 307/38
USPC .................................... 524/879; 549/472, 491
See application file for complete search history.

(56) References Cited

U.S. PATENT DOCUMENTS

| 3,729,405 A | * | 4/1973 | De Schrijver | 522/46 |
| 4,303,924 A | | 12/1981 | Young, Jr. | |
| 4,978,969 A | | 12/1990 | Chieng | |
| 5,270,368 A | | 12/1993 | Lent et al. | |
| 5,623,001 A | | 4/1997 | Figov | |
| 5,844,020 A | | 12/1998 | Paine et al. | |
| 5,952,402 A | | 9/1999 | Paine et al. | |
| 6,042,227 A | | 3/2000 | Meinhardt et al. | |
| 6,825,315 B2 | | 11/2004 | Aubert | |

OTHER PUBLICATIONS

Luo, X. et al.; "A Thermally Responsive, Rigid, and Reversible Adhesive," Polymer, 51, 1169-75 (2010).*
Aubert, J.H., "Thermally Removable Epoxy Adhesives Incorporating Thermally Reversible Diels-Alder Adducts," J. Adhesion, 79, 609-616 (2003).*
Luo, X. et al., "A Thremally Responsive, Rigid, and Reversible Adhesive," *Polymer,* 51, 1169-75 (2010).
Wouters, M. et al., "Tuneable Adhesion Through Novel Binder Technologies," *Prog. Org. Coatings,* 72, 152-158 (2011).

* cited by examiner

*Primary Examiner* — Kelechi Egwim
(74) *Attorney, Agent, or Firm* — Pillsbury Winthrop Shaw Pittman LLP

(57) ABSTRACT

A composition includes a reversible polymer material, which can reversibly transition between a liquid state and a solid state by reversible cycloaddition reactions, wherein upon cooling, the reversible polymer material transitions from a liquid state to a solid state by reversible cycloaddition reactions within a time period of less than about 10 seconds.

20 Claims, 2 Drawing Sheets

REVERSIBLE POLYMER COMPOSITION

TECHNICAL FIELD

The present disclosure is generally directed to a reversible polymer composition comprising a reversible polymer material that can reversibly transition between a liquid state and a solid state by reversible cycloaddition reactions and that in the solid state forms a hard polymer film.

BACKGROUND

Reversible Diels-Alder based polymers are generally known, and have been investigated for use in solid ink printing. These are disclosed, for example, in U.S. Pat. Nos. 5,844,020, 5,952,402, and 6,042,227. These reversible Diels-Alder based polymers would be particularly useful in ink jet applications, because the ink jet apparatus allows for precise, imagewise control of the placement of material, and thus would allow for the production of precise, hard polymer films possessing the reversible solid-to-liquid conversion properties.

However, the Diels-Alder based polymers previously investigated suffered from long solidification times after being deposited on a substrate. For example, it was found that many of the prior Diels-Alder based polymers had solidification times on the order of several hours, making them unsuitable for use in most printing applications. Long solidification times are unsuitable because while the printed material remains in a liquid or semi-liquid state, the image can become distorted, image quality can degrade, and the printed images cannot be stacked on top of each other resulting in either large space needs or low throughput.

Accordingly, there is a need for improved materials that exhibit the reversible polymerization property, but that have shorter solidification times to permit their efficient and economical use in commercial processing, such as in conventional ink jet printing. There is also a need for a hard polymer material that can be formed from a liquid having very low melt viscosity, such that it may be suitable for jetting at typical ink jet operating temperatures and in a precise imagewise fashion.

SUMMARY

The present disclosure in embodiments addresses the above and other needs by providing a composition, such as can be suitably used in ink jet printing, where the composition comprises a reversible polymer material that can transition from a liquid state to a solid that this is a hard polymer film.

More particularly, the present disclosure provides a composition comprising a reversible polymer material, which can reversibly transition between a liquid state and a solid state by reversible cycloaddition reactions, wherein upon cooling, the reversible polymer material transitions from a liquid state to a solid state by reversible cycloaddition reactions within a time period of less than about 10 seconds.

In another embodiment, the present disclosure provides a method of making a polymer film, comprising:

applying a composition comprising a reversible polymer material, which can reversibly transition between a liquid state and a solid state by reversible cycloaddition reactions, to a substrate in a liquid state; and cooling the composition, wherein upon cooling, the reversible polymer material transitions from a liquid state to a solid state by reversible cycloaddition reactions within a time period of less than about 10 seconds.

DETAILED DESCRIPTION

Figure 1A:
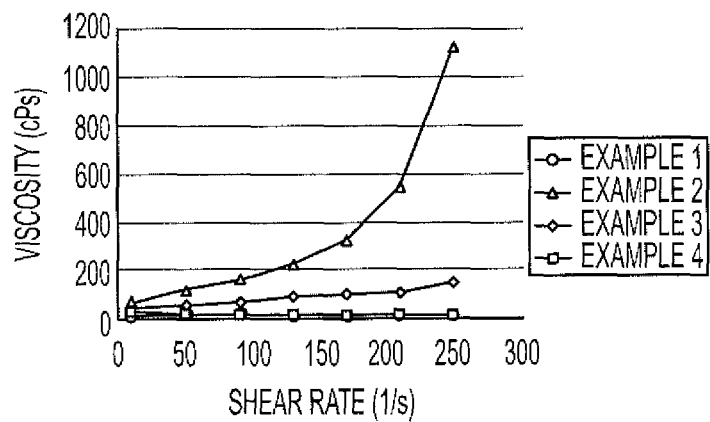
FIG. 1A and FIG. 1B show viscosity properties of coatings according to the Examples.

The present disclosure provides compositions comprising a reversible polymer material. The compositions comprise a reversible polymer material formed from constituent materials based on Diels Alder chemistry, which can quickly reversibly transition between a liquid state and a solid state by reversible cycloaddition reactions. The compositions can be used in a variety of applications where it is desirable to form a hard polymer film. In embodiments, the compositions are especially suitable for use in ink jet printers, where the ink jet printer can eject the liquid composition material in an imagewise fashion, and the composition can then solidify to form a hard polymer film of the desired image. Thus, for example, the compositions can be suitably used in digital image processing to form hard polymer films, to form hard polymer overcoats to protect an underlying image, to form a hard polymer interface between two materials, and the like.

In the heated liquid state, the composition is preferably a low viscous liquid that can be readily applied by a variety of coating methods, such as spraying, coating, ink jetting, and the like. Upon cooling, the composition quickly undergoes reversible cycloaddition reactions that convert the liquid composition into a cured polymer film.

Composition

The composition includes as an essential component a reversible polymer material, which can reversibly transition between a liquid state and a solid state by reversible cycloaddition reactions. In embodiments, the reversible polymer is formed from constituent materials based on Diels Alder chemistry. These materials are "curable" in that they can be deposited on a substrate in a liquid state, making them suitable for such deposition methods as spraying, coating, ink jet printing, and the like. The materials have end groups suitable for Diels Alder cycloadditions and co-exist in the molten or liquid state as a very low viscosity liquid. However, as the materials are cooled, cycloaddition takes place, resulting in hard polymers with excellent film forming and adhesion characteristics. The reversible polymer material is thus particularly useful in ink jet printing applications because it can be easily jetted while in the molten state, but form a hard polymer when solidified. The reversible nature of the reaction also allows the composition to be repeatedly heated and cooled in the printing apparatus to match printing demand.

Reverse Diels-Alder based polymers are generally known, and have been investigated for use in solid ink printing, as exemplified for example by U.S. Pat. Nos. 5,844,020, 5,952,402, and 6,042,227. However, the Diels-Alder based polymers previously investigated suffered from long solidification times after being deposited on a substrate. For example, it was found that many of the prior Diels-Alder based polymers had solidification times on the order of several hours, making them unsuitable for use in most printing applications.

Long solidification times are unsuitable because while the printed material remains in a liquid or semi-liquid state, the image can become distorted, image quality can degrade, and the printed images cannot be stacked on top of each other resulting in either large space needs or low throughput.

In contrast, the reversible polymer materials of the present disclosure have solidification times on the order of seconds, making them more suitable for use in printing and imaging applications and for forming hard polymer films of a desired shape or image. Due to the faster solidification times, the deposited polymer films retain their high quality image, substrates with deposited polymer films can be stacked on top of each other, and faster throughput can be achieved. Thus, in embodiments, the solidification time of the reversible polymer material is less than about 10 seconds, such as less than about 5 seconds or less than about 3 seconds. For example, the solidification time for the reversible polymer material can be from about 0.01 second or from about 0.05 second or from about 0.1 second to about 0.5 second or about 1 second or about 5 seconds. By "solidification" herein it is meant that the sample is hardened and emits an audible clicking sound when tapped with a spatula. For example, when samples are prepared as films not exceeding 5 mm in thickness, the rate of cooling is very fast and does not play a role in the solidification times of each of the samples. In these samples, the solidification time is taken to be the time after the rapid cooling to ambient or room temperature. The degree of polymerization can also be measured using $^1$H NMR spectroscopy, although it has been found that the degree of polymerization does not necessarily correlate with solidification times.

To achieve these faster solidification times, embodiments of the present disclosure utilize reversible polymer materials that are formed from maleimides and furans, with varying linking chemistry. The maleimides and furans can be in any form, such as bismaleimides and bisfurans, trigonal maleimides and trigonal furans, and the like. The linking groups can vary in length and chemistry and can include, for example, linear or branched alkyl groups, cyclic alkyl groups, aryl groups, arylalkyl groups, alkylaryl groups, alkylenedioxy groups, and the like, all of which can be substituted or unsubstituted. Although not limited, it is believed that as the size of linking group increases, the solidification time increases. For example, as the number of carbon atoms in the linking group increases, or as the number of oxygen atoms (such as in alkyleneoxy groups) in the linking group increases, the solidification time also tends to increase. Of course, it still may be possible to use compounds with otherwise slower solidification times, for example, if they are used in combination with other materials having a faster solidification time.

For example, suitable bismaleimides and bisfurans are represented by the following structures:

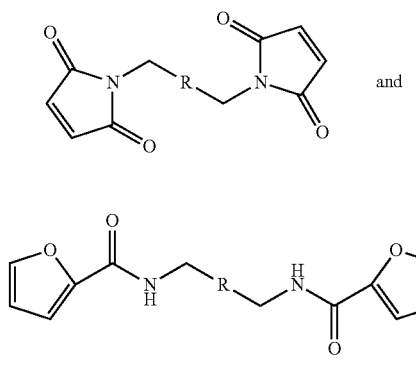

where R is the linking group. For example, R can be an alkyl group, such as a linear alkyl group having from 1 or from about 2 to about 20 carbon atoms, from about 3 to about 15 carbon atoms, or from about 4 or about 5 or about 6 carbon atoms to about 8 or about 10 or about 12 carbon atoms; a cyclic alkyl group such as a cyclic alkyl group having about 5 or about 6 carbon atoms to about 8 or about 10 carbon atoms; an aryl group such as a phenyl group or a naphthyl group; an alkylenedioxy group having from 1 or from about 2 to about 20 carbon atoms, or from about 2 to about 10 carbon atoms, or from about 3 to about 8 carbon atoms, such as an ethylenedioxy group; or the like.

In other embodiments, trigonal structures can be used. For example, suitable trigonal maleimides and furans are represented by the following structures:

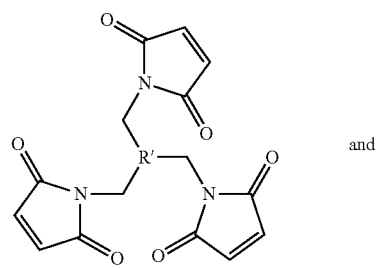

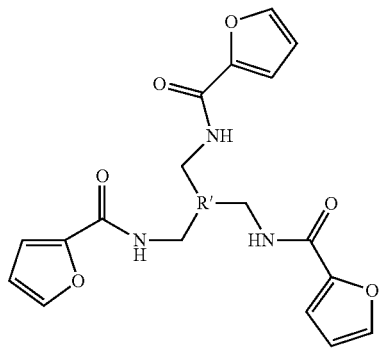

where R' is $NR_3$, where each R is the same or different and is the linking group as defined above. Specific embodiments of the trigonal maleimides and furans where R' is $N(CH_2)_3$— are represented by the following structures:

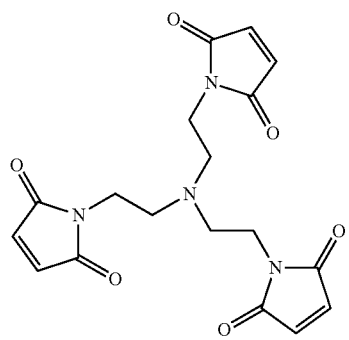

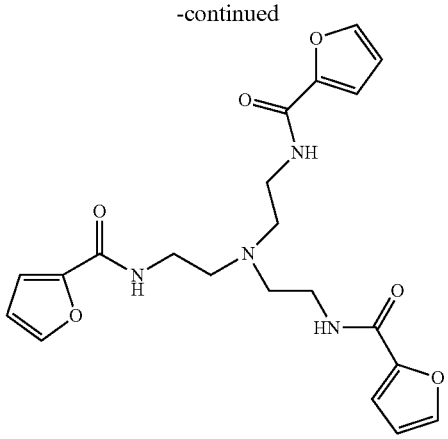

In still other embodiments, other forms of maleimides and furans can be used, and it will be understood that the present disclosure is not limited to bis- or tris-structures.

The maleimides and furans can be made by reactions known in the art, modified as will be apparent to incorporate desired linking groups. For example, the bismaleimides can be readily prepared by reacting maleic anhydride with a suitable reactant such as a diamino compound. In a similar manner, the bisfurans can be readily prepared by reacting 2-furoyl chloride with a suitable reactant such as a diamino compound. In one embodiment, where the diamino compound is a diaminoalkane, such as diaminooctane, the bismaleimide and bisfuran can be prepared as follows:

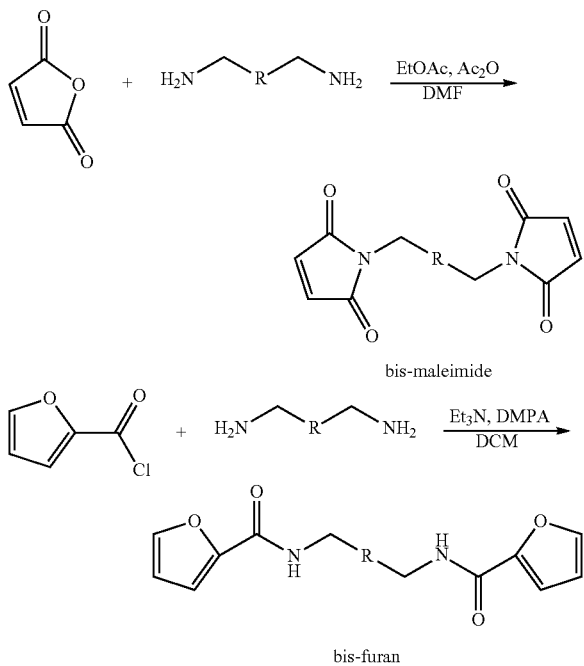

where R is the linking group as described above. Similar reaction schemes can be used to prepare the trigonal maleimides and furans.

So that the Diels-Alder cycloaddition reactions can proceed, the reversible polymer material in embodiments includes a mixture of maleimide monomer units or species and furan monomer units or species. Heating the solid maleimide/furan mixture above its melting point results in very low viscosity liquids. However, cooling of the mixtures promotes Diels-Alder coupling, resulting in the formation of polymers. Heating the polymers above the melting point of the constituent maleimide and furan species reverses the process, re-generating the low viscosity liquid. This reversible transition of the materials from monomer units or species to polymer is exemplified for one set of materials by the following reaction scheme:

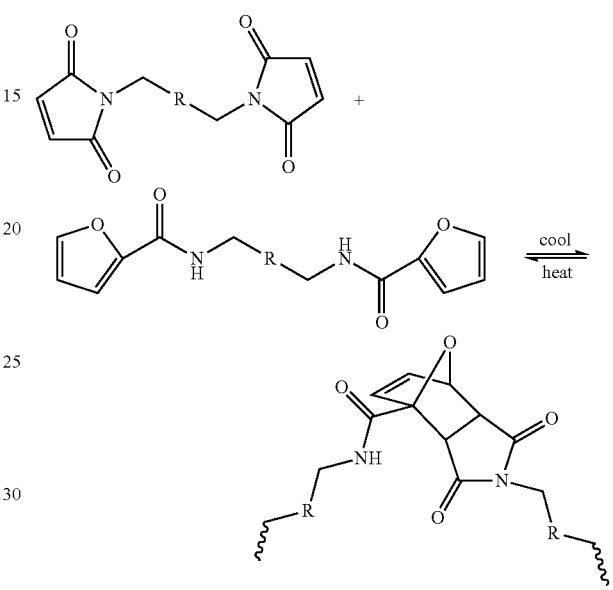

In forming the mixture of maleimide monomer units or species and furan monomer units or species, it is desired in embodiments that the materials be in approximately equimolar amounts of functional groups. Thus, for example, where the mixture is formed from bismaleimides having two reactive functional groups and bisfurans having two reactive functional groups, the bismaleimides and bisfurans are desirably present in a molar ratio of about 1:1, such as from about 1.5:1 to about 1:1.5, or from about 1.3:1 to about 1:1.3, from about 1.2:1 to about 1:1.2, or from about 1.1:1 to about 1:1.1. Similarly, where the mixture is formed from trigonal maleimides having three reactive functional groups and trigonal furans having three reactive functional groups, the trigonal maleimides and trigonal furans are desirably present in a molar ratio of about 1:1, such as from about 1.5:1 to about 1:1.5, or from about 1.3:1 to about 1:1.3, from about 1.2:1 to about 1:1.2, or from about 1.1:1 to about 1:1.1. However, where the mixture is formed from bismaleimides having two reactive functional groups and trigonal furans having three reactive functional groups, or from trigonal maleimides having three reactive functional groups and bisfurans having two reactive functional groups, the maleimides and furans are desirably present in a molar ratio of the trigonal material to the bis material of about 2:3, such as from about 2.5:3 to about 2:2.5, or from about 2.3:3 to about 2:2.7, from about 2.2:3 to about 2:2.8, or from about 2.1:3 to about 2:2.9. Although other ratios of the materials can be used, the reversible polymer material will have too much residual liquid material if the ratio of materials diverges too far from being equimolar. That is, as the ratio becomes unbalanced, there will be too much of one constituent material to react with the other material to form the reversible polymer in the solid state. The excess unreacted material will therefore only serve to dilute the coupled reversible polymer and compromise its mechanical integrity.

Although not required, it is also desired in embodiments that the materials used to form the mixture have the same linking group, or at least the same general type of linking group. Where the mixture is formed from the depicted maleimides and furans shown above, it is desirable that the maleimides and furans have the same linking group R, or at least the same type of linking group R. Thus, for example, the linking group of the maleimides and furans in embodiments is each an alkyl group, such as each a linear alkyl group of the same chain length; is each a cyclic alkyl group such as each a cyclic alkyl group having the same structure and number of carbon atoms; is each an aryl group, such as each a phenyl group; is each an alkylenedioxy group such as each an ethylenedioxy group; or the like. Mixtures of different spacer groups can be accommodated, provided the chemistries in each of the spacer groups are compatible with one another, such that the two compounds are miscible in each other. For example, mixtures having very dissimilar polarities would be inappropriate, as the two reagents would be unstable and would undergo phase separation. Of course, if desired, different linking groups can be used in the materials.

Similarly, in embodiments it is desired that the materials used to form the mixture be one form of maleimide and one form of furan. This allows the Diels-Alder reaction to more rapidly progress because the counter functional groups of the materials are more closely positioned to each other in the mixture. However, if desired, more than one type of maleimide and/or more than one type of furan can be used in forming the mixture. Thus, for example, the mixture can be formed from one type of maleimide and one type of furan, or can be formed from one, two, three, or more different maleimides and one, two, three, or more different furans, to provide desirable properties of both the liquid mixture and the solid reversible polymer.

In forming the mixture, the mixture contains at least the reversible polymer material, such as the mixture of the maleimide monomer units or species and furan monomer units or species. Because the ability of the monomers to react together by Diels-Alder cycloaddition reactions is dependent upon the materials readily contacting each other, it is desired that as few additional ingredients as possible be included in the mixture. Thus, for example, in one embodiment the mixture consists entirely of only the maleimide monomer units or species and furan monomer units or species; in other embodiments, the mixture consists essentially of the maleimide monomer units or species and furan monomer units or species, plus additional materials that do not interfere with the ability of the monomers to react to form the reversible polymer material. In still other embodiments, additional components may be included for other intended purposes. Of course, it will be appreciated in each of these variants that the mixture may also include incidental impurities and the like. Where additional materials are included in the mixture in addition to the maleimides and furans, the maleimides and furans can together be present in the mixture in a majority amount, such as from about 50, about 60, about 70, or about 80 to about 90, about 95, or about 100 percent by weight, or the maleimides and furans can together be present in the mixture in a minority amount, such as from about 1, about 5, about 10, or about 20 to about 30, about 40, or about 50 percent by weight, based on a total weight of the composition including the mixture.

If desired, the composition can include other additives for their conventional purposes. For example, the composition can include one or more of light stabilizers, UV absorbers (which absorb incident UV radiation and convert it to heat energy that is ultimately dissipated), antioxidants, optical brighteners (which can improve the appearance of the image and mask yellowing), thixotropic agents, dewetting agents, slip agents, foaming agents, antifoaming agents, flow agents, waxes, oils, plasticizers, binders, electrical conductive agents, organic and/or inorganic filler particles, leveling agents (agents that create or reduce different gloss levels), opacifiers, antistatic agents, dispersants, colorants (such as pigments and dyes), biocides, preservatives, and the like. However, additives may negatively affect the speed and degree of the reversible cycloaddition reactions, and thus care must be taken when formulating a composition using optional additives.

For example, in some embodiments, it may be helpful to include a radical scavenger in the composition. It has been found that for some reversible polymer mixtures, prolonged heating of the molten liquid can lead to irreversible hardening of the mixture, due to the propensity of maleimide compounds to undergo a 2+2 cycloaddition reaction when exposed to UV light. As a result of the cycloaddition reaction, an irreversible polymerization or hardening of the material can occur, which can render the composition unacceptable for some uses such as in a solid inkjet printer. Adding a radical scavenger to those compositions can thus prevent or significantly slow down the cycloaddition reaction, thereby preventing the irreversible polymerization from occurring, and allowing the molten liquids to maintain their low melt viscosities for a longer period of time.

Where the radical scavenger is to be included, any suitable radical scavenger can be used. Suitable radical scavengers include, for example, sorbitol, methylether hydroquinone, t-butylhydroquinone, hydroquinone, 2,5-di-1-butylhydroquinone, 2,6-di-tert-butyl-4-methyl phenol (or BHT for butylhydroxytoluene), 2,6-di-t-butyl-4-methoxyphenol, nitroxides, 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3, 5-di-tert-butyl-4-hydroxyphenyl)propionate, tetrakis (methylene(3,5-di-tert-butyl)-4-hydroxy-hydrocinnamate) methane, phenothiazines, alkylamidonoisoureas, thiodiethylene bis(3,5,-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide), and naturally occurring antioxidants such as raw seed oils, wheat germ oil, tocopherols, and gums, and mixtures thereof. Suitable nitroxides include, for example, 2,2,6, 6-tetramethyl-1-piperidinyloxy (TEMPO), 2,2,6,6-tetraethyl-1-piperidinyloxy, 2,2,6-trimethyl-6-ethyl-1-piperidinyloxy, 2,2,5,5-tetramethyl-1-pyrrolidinyloxy (PROXYL), dialkyl nitroxide radicals such as di-t-butyl nitroxide, diphenyl nitroxide, t-butyl-t-amyl nitroxide, 4,4-dimethyl-1-oxazolidinyloxy (DOXYL), 2,5-dimethyl-3,4-dicarboxylic-pyrrole, 2,5-dimethyl-3,4-diethylester-pyrrole, 2,3,4,5-tetraphenyl-pyrrole, 3-cyano-pyrroline-3-carbamoyl-pyrroline, 3-carboxylic-pyrroline, 1,1,3,3-tetramethyl-isoindoline-2-yloxyl,1,1,3,3-tetraethylisoindolin-2-yloxyl, porphyrexide nitroxyl radicals such as 5-cyclohexyl porphyrexide nitroxyl and 2,2,4,5,5-pentamethyl-D3-imidazoline-3-oxide-1-oxyl and the like, galvinoxyl and the like, 1,3,3A trimethyl-2-azabicyclo[2,2,2]octane-5-oxide-2-oxide, 1A azabicyclo[3,3,1]nonane-2-oxide, and the like. Substituted variants of these radical scavengers can also be used, such as 4-hydroxy-TEMPO, 4-carboxy-TEMPO, 4-benzoyloxy-TEMPO, 4-methoxy-TEMPO, 4-carboxylic-4-amino-TEMPO, 4-chloro-TEMPO, 4-hydroxylimine-TEMPO, 4-oxo-TEMPO, 4-oxo-TEMPO-ethylene ketal, 4-amino-TEMPO, 3-carboxyl-PROXYL, 3-carbamoyl-PROXYL, 2,2-dimethyl-4,5-cyclohexyl-PROXYL, 3-oxo-PROXYL, 3-hydroxylimine-PROXYL, 3-aminomethyl-PROXYL, 3-methoxy-PROXYL, 3-t-butyl-PROXYL, 3-maleimido-PROXYL, 3,4-di-t-butyl-PROXYL, 3'-carboxylic-PROXYL, 2-di-t-butyl-DOXYL, 5-decane-DOXYL, 2-cyclohexane-DOXYL, and the like.

Optionally, many commercial antioxidant stabilizers function by trapping free radicals and thus may be used as a radical scavenger. For example, IRGASTAB® UV 10 is a nitroxide and may suitably be used. Other suitable compounds may include, for example, NAUGARD® 524, NAUGARD® 635, NAUGARD® A. NAUGARD® 1-403, and NAUGARD® 959, commercially available from Crompton Corporation, Middlebury, Conn.; NAUGARD® 76. NAUGARD® 445, and NAUGARD® 512 commercially available by Uniroyal Chemical Company; IRGANOX® 1010 and IRGASTAB® UV 10, commercially available from Ciba Specialty Chemicals; GENORAD™ 16 and GENORAD™ 40 commercially available from Rahn A G, Zurich, Switzerland, and the like, as well as mixtures thereof.

The radical scavenger may be present in the composition in any effective amount. For example, it may be present in an amount of from about 0.01% to about 15% by weight of the composition, such as from about 0.05% to about 12% by weight of the composition, from about 0.1% to about 10% by weight of the composition, or from about 1% to about 8% or about 2% to about 5% by weight of the composition.

In the molten state, where the composition is heated to above the melting point of the reverse polymer material, the composition is a very low viscosity liquid. For example, the liquid composition has a viscosity of from about 1 to about 100 cPs, such as from about 1 to about 50 cPs, from about 2 or from about 5 to about 10 or about 15 cPs at a temperature above the melting point of the reverse polymer material. For example, in one embodiment, and for use in an ink jet printing apparatus, it is desired that the liquid composition has a viscosity of from about 1 to about 100 cPs, such as from about 1 to about 50 cPs, from about 1 or from about 2 to about 30 or about 40 cPs, or from about 2 to about 20 cPs, at a temperature of from about 60 to about 140° C., such as from about 65 or from about 70 to about 125 or about 130° C., such as from about 75 to about 120° C. However, as the composition is cooled, cycloaddition takes place, resulting in a hard polymer with excellent film forming and adhesion characteristics.

Composition Application Methods

The compositions of the present disclosure can be used in a wide variety of applications where it is desired to form a hard polymer film. The compositions are particularly useful in digital image processing applications, such as ink jet printing, because the low viscosity properties of the composition in the liquid state make the compositions amendable to ink jet printing. This allows precise shapes or images of the composition to be formed based on digital printing processes, where the printed liquid composition hardens or cures into a hard polymer film of desired shape or image. Of course, other application methods can also be used, such as spraying, coating, dipping, and the like, depending upon the desired use and end-product.

When the composition is applied onto a substrate using digital ink jet printing, it can be applied at any desired thickness and amount. The composition can be applied in at least one pass over the substrate, or it can be applied as multiple, at least partially overlapping passes over the substrate.

The substrate employed can be any appropriate substrate depending upon the end use of the product. Exemplary substrates include, but are not limited to, plain paper, coated paper, plastics, polymeric films, treated cellulosics, wood, xerographic substrates, metal substrates, and mixtures thereof, optionally comprising additives coated thereon. The optional additives include, but are not limited to, anti-curl compounds, such as, for example, trimethylolpropane; and mixtures thereof; and any other optional additives well known in the ink art or xerographic art for enhancing the performance and/or value of the ink and/or substrate. The resultant polymer film can be retained as adhered to the substrate, or in embodiments the resultant polymer film can be removed from the substrate such as by peeling or the like.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

General Procedure for Synthesis of Bismaleimides

In a 500 mL RBF (round-bottomed flask) equipped with a magnetic stir bar was dissolved maleic anhydride (10.5 eq) in 75 mL DMF (dimethylformamide). The resulting solution was chilled on ice and the 1,8-octanediamine (5 eq) dissolved in DMF (75 mL) was added dropwise over ~20 min. The ice bath was removed, and sodium acetate (1 eq) and acetic anhydride (11 eq) were added in one portion, and the mixture stirred overnight at 50° C. The mixture turned dark brown within 30 minutes of the addition of NaOAc and Ac$_2$O. DMF was removed by vacuum distillation (60° C.), and DCM (dichloromethane) (150 mL) was added to the dark brown mixture. The organic layer was extracted with NaHCO$_3$ (5×100 mL), dried over MgSO$_4$, and the solvent removed under vacuum. The resulting compounds were purified by column chromatography.

1,1'-(octane-1,8-diyl)bis(1H-pyrrole-2,5-dione) (denoted M1): The general procedure was carried out using maleic anhydride (14.27 g, 146 mmol), 1,8-octanediamine (10.0 g, 69.3 mmol), sodium acetate (1.14 g, 13.9 mmol) and acetic anhydride (15.57 g, 153 mmol). The resulting compound was purified by column chromatography (98:2 DCM:EtOAc), and the product obtained as a white solid (5.2 g/25%).

1,1'-(cyclohexane-1,3-diylbis(methylene))bis(1H-pyrrole-2,5-dione) (denoted M2): The general procedure was carried out using maleic anhydride (20.59 g, 210 mmol), 1,3-cyclohexanebis(methylamine) (14.22 g, 100 mmol), sodium acetate (1.64 g, 20 mmol), and acetic anhydride (22.46 g, 220 mmol). The resulting compound was purified by column chromatography (98:2 DCM:EtOAc), and the product obtained as a white solid (3.55 g/12%).

1,1'-(1,3-phenylenebis(methylene))bis(1H-pyrrole-2,5-dione) (denoted M3): The general procedure was carried out using maleic anhydride (20.59 g, 210 mmol), m-xylylenediamine (13.62 g, 100 mmol), sodium acetate (1.64 g, 20 mmol), and acetic anhydride (22.46 g, 220 mmol). The resulting compound was purified by column chromatography (97:3 DCM:EtOAc), and the product obtained as a white solid (6.51 g/22%).

1,1'-((ethane-1,2-diylbis(oxy))bis(ethane-2,1-diyl))bis (1H-pyrrole-2,5-dione) (denoted M4): The general procedure was carried out using maleic anhydride (13.23 g, 135 mmol), 2,2'-(ethylenedioxy)bis(ethylamine) (10.0 g, 67.5 mmol), sodium acetate (1.11 g, 13.5 mmol), and acetic anhydride (15.15 g, 148 mmol). The resulting compound was purified by column chromatography (95:5 DCM:EtOAc), and the product obtained as a white solid (4.5 g/22%).

1,1',1''-(nitrilotris(ethane-2,1-diyl))tris(1H-pyrrole-2,5-dione) (denoted M5): In a 500 mL round-bottomed flask under argon was dissolved maleic anhydride (20.1 g, 205 eq) in 75 mL DMF. The resulting solution was chilled on ice and then tris(2-aminoethyl)amine (10.0 g, 68.4 mmol) dissolved in DMF (75 mL) was added dropwise over ~20 min. The ice bath was removed, and sodium acetate (1.68 g, 20.52 mmol) and acetic anhydride (23.04 g, 226 mmol) were added in one portion, and the mixture stirred overnight at 50° C. The mixture turned dark brown within 30 minutes of the addition of NaOAc and Ac$_2$O. DMF was removed by vacuum distillation (60° C.), and DCM (150 mL) was added to the dark brown mixture. The organic layer was extracted with NaHCO$_3$ (5×100 mL), dried over MgSO$_4$, and the solvent removed under vacuum. The resulting compound was purified by column chromatography (95:5 DCM:EtOAc), to yield a light yellow solid (8.0 g, 30%).

General Procedure for Synthesis of Bisfurans

To a 500 mL RBF equipped with a magnetic stir bar was added the 1,8-octanediamine (47.9 eq), triethylamine (95.7 eq), DMAP (4-Dimethylaminopyridine) (1 eq) and DCM (200 mL). The solution was chilled on ice, then furoyl chloride (100 eq) in DCM (50 mL) was added dropwise. The ice bath was removed, and the mixture stirred at room temperature overnight. The organic layer was extracted with NaHCO$_3$ (5×100 mL), dried over MgSO$_4$, and the solvent removed under vacuum. The resulting compounds were purified by column chromatography.

N,N'-(octane-1,8-diyl)bis(furan-2-carboxamide) (denoted F1): The general procedure was carried out using 1,8-octanediamine (10.0 g, 69.3 mmol), triethylamine (14.2 g, 141 mmol), DMAP (0.17 g, 1.35 mmol) and furoyl chloride (19.0 g, 146 mmol). The resulting compound was purified by column chromatography (98:2 DCM:EtOAc), and the product obtained as a white solid (21.5 g/92%).

N,N'-(cyclohexane-1,3-diylbis(methylene))bis(furan-2-carboxamide) (denoted F2): The general procedure was carried out using 1,3-cyclohexanebis(methylamine) (10.0 g, 70.3 mmol), triethylamine (14.2 g, 141 mmol), dimethylaminopyridine (0.17 g, 1.41 mmol), and furoyl chloride (19.0 g, 146 mmol). The resulting compound was purified by column chromatography (95:5 DCM:EtOAc), and the product obtained as a white solid (3.5 g/15%).

N,N'-(1,3-phenylenebis(methylene))bis(furan-2-carboxamide) (denoted F3): The general procedure was carried out using m-xylylenediamine (10.0 g, 73.4 mmol), triethylamine (14.9 g, 147 mmol), dimethylaminopyridine (0.17 g, 1.41 mmol), and furoyl chloride (20.13 g, 154 mmol). The resulting compound was purified by column chromatography (95:5 DCM:EtOAc), and the product obtained as a white solid (21.8 g/92%).

N,N'-((ethane-1,2-diylbis(oxy))bis(ethane-2,1-diyl))bis (furan-2-carboxamide) (denoted F4): The general procedure was carried out using 2,2'-(ethylenedioxy)bis(ethylamine) (10.0 g, 67.5 mmol), triethylamine (13.66 g, 135 mmol), dimethylaminopyridine (0.17 g, 1.41 mmol), and furoyl chloride (18.5 g, 142 mmol). The resulting compound was purified by column chromatography (95:5 DCM:EtOAc), and the product obtained as a white solid (10.9 g/48%).

N,N',N''-(nitrilotris(ethane-2,1-diyl))tris(furan-2-carboxamide) (denoted F5): In a 500 mL RBF under argon was added the 1,8-octanediamine (10.0 g, 68.4 mmol), triethylamine (20.76 g, 205 mmol), DMAP (0.68 g, 20.5 mmol) and DCM (350 mL). The solution was chilled on ice, then furoyl chloride (27.7 g, 212 mmol) in DCM (150 mL) was added dropwise. The ice bath was removed, and the mixture stirred at room temperature overnight. The organic layer was extracted with NaHCO$_3$ (5×100 mL), dried over MgSO$_4$, and the solvent removed under vacuum. The resulting compound was purified by column chromatography (99:1 DCM:EtOAc) to yield a white solid (16.1 g, 82%).

The bismaleimides M1 to M4 and bisfuran F1 to F4 prepared above are represented by the following structures were formed, where R the linking group R is varied as shown:

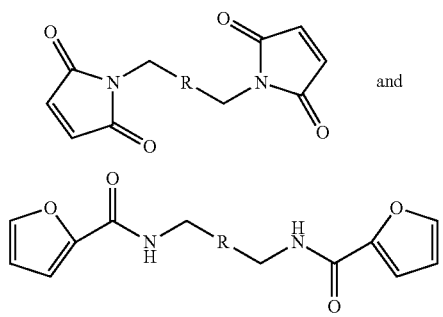

| Compound | R |
|---|---|
| M1, F1 | ~~~~~~~~ |
| M2, F2 | (cyclohexane) |
| M3, F3 | (phenylene) |
| M4, F4 | ~O~~O~ |

The trigonal maleimide M5 and trigonal furan F5 are represented by the following structures:

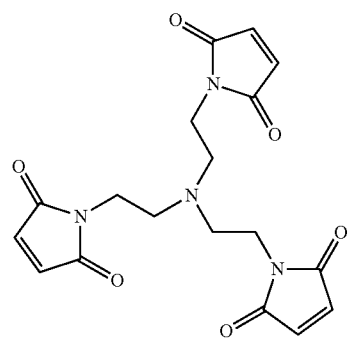

-continued

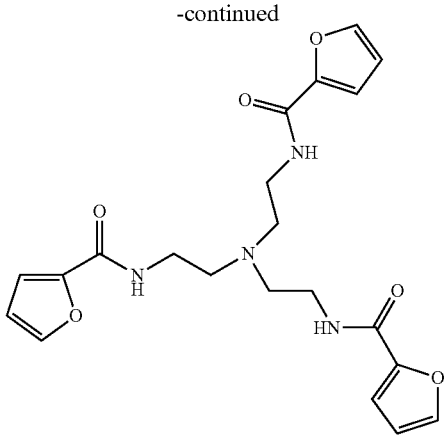

Example 1

A mixture of the pairs of maleimide and furan M1 and F1 was made by mixing the maleimide and the furan on about a 1:1 molar basis. The sample was used for the following testing and analysis.

Examples 2-5

Similar to Example 1, mixtures of the pairs of maleimides and furans (M2 and F2, M3 and F3, M4 and F4, M5 and F5) were made by mixing the maleimide and the respective furan on about a 1:1 molar basis. The samples were used for the following testing and analysis.

Analysis

The testing showed that heating the solid maleimide/furan mixtures above their melting points resulted in very low viscosity liquids, while cooling of the mixtures resulted in Diels-Alder coupling, resulting in the formation of polymers. Heating the polymers above the melting point of the constituent maleimide/furan reverses the process, re-generating the low viscosity liquid. The reversibility of the process was verified by $^1$H NMR spectroscopy and DSC.

Figure 1B:
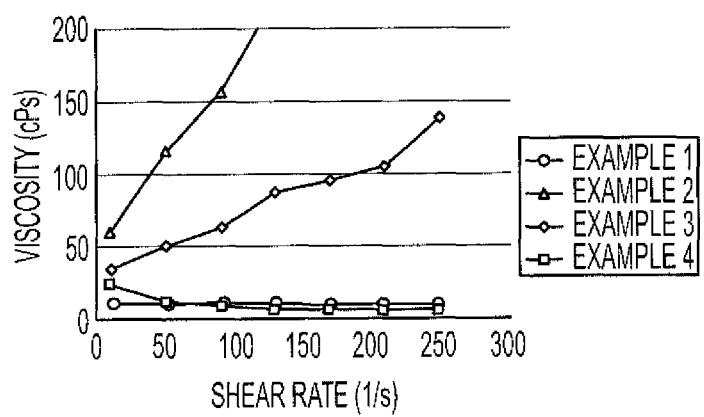

The mixtures were then heated to above their melting points to measure the viscosity behavior of the mixtures. The mixture of Example 1 (mixture of M1 and F1) was heated to 120° C.; the mixture of Example 2 (mixture of M2 and F2) was heated to 190° C.; the mixture of Example 3 (mixture of M3 and F3) was heated to 150° C.; and the mixture of Example 4 (mixture of M4 and F4) was heated to 90° C. Viscosities were measured using an AR 2000 viscometer, available from TA Instruments. Measurements were made at 100 s$^{-1}$ for 25 minutes, using a 25 mm plate assembly, set at a gap width of 200 μm. The results are shown in FIGS. 1A and 1B, where FIG. 1B is a magnified scale of a portion of FIG. 1A. The dilatant behavior of the mixtures of Examples 3 and 4 is believed to be due to the higher temperatures required for melting and viscosity measurement of these particular mixtures, which resulted in an irreversible cross-linking reaction.

Polymer films were cast using samples of the neat, molten monomers mixtures, and the polymer films were allowed to cool. Hardness and modulus were measured directly on these films using a Hysitron Triboindenter®. Samples were prepared by transferring the powder mixture (~50 mg) to a steel sample disc (15 mm diameter). The disc was placed on a hotplate that was pre-heated approximately 20° C. above the melting point of the mixture. Air bubbles that appeared during melting were removed by agitation of the liquid with a clean spatula. The sample discs were removed from the heat source and stored at 60° C., resulting in smooth films with relatively flat surfaces. Samples were allowed to equilibrate at room temperature for 1 h before measurements were made. A 10-2-10 load function was used (10 second load time, 2 second hold, and 10 second unload time) with a maximum load of 1000 N. Measurements were made in 3×3 grids, with a spacing of 15 μm between each indentation. Three separate locations spaced at least 1 mm apart were used on each sample stub. Hardness and modulus values were determined by the Triboscan® software, and reported as an average of these 27 measurements. Control samples (PMMA, quartz) were measured before and after each set of measurements to ensure that measurements were within 5% of their expected values.

Figure 2A:
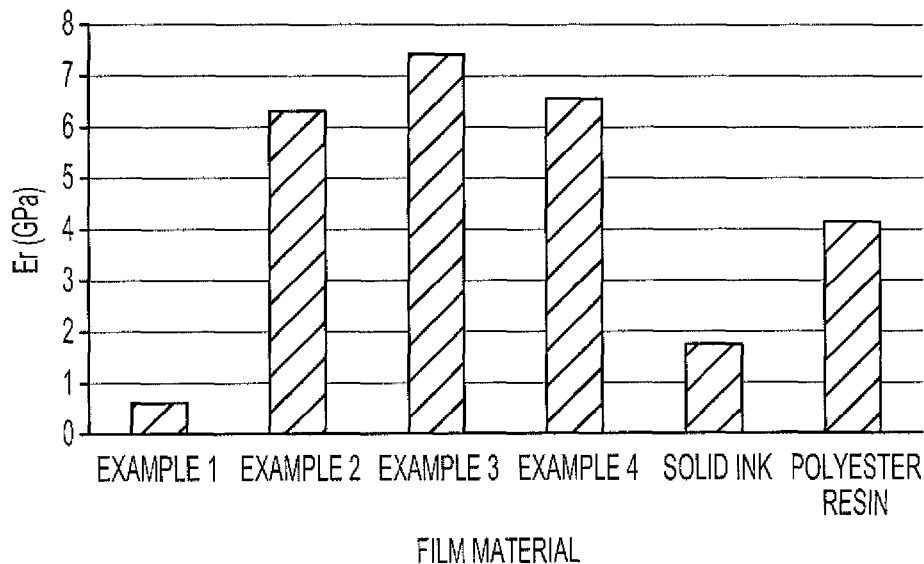
FIG. 2A and FIG. 2B show rheological data of coatings according to the Examples.
Figure 2B:
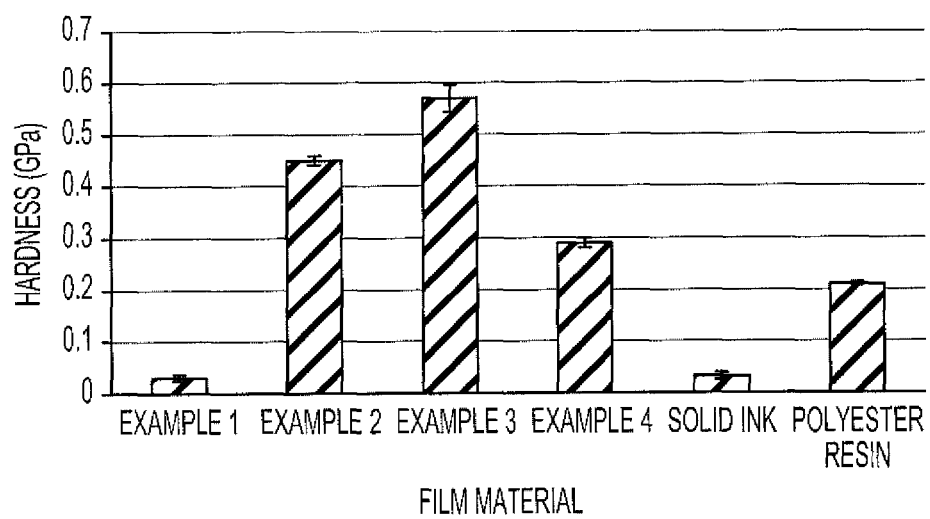

The results are shown in FIGS. 2A and 2B, where FIG. 2A shows the reduced modulus and FIG. 2B shows the hardness of the polymer films made from the mixtures. For comparison purposes, FIGS. 2A and 2B also include measurements for polymer films formed from a solid ink used in the Xerox COLORQUBE® printers and a polyester resin used to form toner particles for use in conventional copiers and printers such as the Xerox DC700 machine.

The quality of the films was also assessed for clarity, hardness and brittleness by visual inspection of the films. The assessment was made to assess the effect of spacer group on the final polymer films. The results of the assessment are provided in the following table.

| Film Composition | Visual Inspection |
|---|---|
| Example 1 | The linear alkyl chain resulted in very brittle, opaque films, believed to be due to the crystallinity of the spacer group. The film exhibited crystallinity. |
| Example 2 | The cyclohexyl spacer gave a clear film, but the film was still very brittle with apparent cracks. The film was amorphous. |
| Example 3 | The phenyl spacer gave a clear film, but the film was still very brittle with apparent cracks. The film was amorphous. |
| Example 4 | The diethyleneoxy spacer gave a very durable, clear polymer film that was considerably less brittle than the other three materials. The film was amorphous. |

The above testing demonstrates that the phenyl spacer group in Example 3 provided the hardest material of those tested, although the polymer film was quite brittle. Example 4, having a diethyleneoxy spacer, formed a polymer film that was slightly softer, but was much less brittle, as compared to Example 3. Nonetheless, all of the films formed from the materials of Examples 1-4 were considerably harder than the conventional toner resin, and dramatically harder than the conventional solid ink.

Solidification time was also found to be dependent upon the spacer chemistry of the materials. Attempts to measure the solidification time were made using Time Resolved Optical Microscopy (TROM); however, these attempts were unsuccessful because only the film of Example 1 displayed any degree of crystallinity while the remaining three films were all amorphous and thus were not visible by the optical methods used in the TROM technique. Instead, simple tapping of the films with a spatula was used, where an audible click was denoted as complete solidification of the polymer. In this testing, the films of both Example 1 and Example 4 took several hours to completely harden, while films of Example 2 and Example 3 solidified in seconds. A combination of the materials was also tested for solidification time, and it was found that an 80:20 mixture of Example 4 and Example 3 resulted in a clear, non-cracking film that hardened within minutes.

Example 6

Image testing was conducted using the materials of Example 4. In this Example, a K-Proof was prepared using the monomers of Example 4, with added 2% by weight Orasil Blue GN dye for visualization. For comparison, a K-Proof was also using the solid ink. The K-Proofs were applied to coated paper (Xerox Digital Color Elite Gloss, 120 gsm) and then tested for image robustness. The images were scratched using the a three-finger gouge system, and another K-proof was folded along with a Xerox Business 4200 (75 gsm) facing page in a Duplo D-590 folder and evaluated for fold crease. Evaluation was made using a Site Index Reference (SIR) rating system using the Xerox COLORQUBE® ink as the reference image. Samples were rated on a scale from 1 to 5 for the defect being evaluated, with a rating of 1 representing an exceptional level, a rating of 2 representing a good level, a rating of 3 representing a marginal/acceptable level, a rating of 4 representing a poor level, and a rating of 5 being completely unacceptable. The results were as follows:

|  | Scratch | Fold Crease | Fold Offset | Crock Rub on Cloth |
|---|---|---|---|---|
| Example 4 | 1.5 | 1 | 1 | 2 |
| Ink | 5 | 5 | 2.5 | 5 |

It will be appreciated that various of the above-disclosed and other features and functions, or alternatives thereof, can be combined into many other different systems or applications. Also, various presently unforeseen or unanticipated alternatives, modifications, variations or improvements therein can be subsequently made by those skilled in the art, and are also intended to be encompassed by the following claims.

What is claimed is:

1. A composition, comprising a reversible polymer material, which can reversibly transition between a liquid state and a solid state by reversible cycloaddition reactions, wherein upon cooling, the reversible polymer material transitions from a liquid state to a solid state by reversible cycloaddition reactions within a time period of less than about 10 seconds.

2. The composition of claim 1, wherein upon cooling, the reversible polymer material transitions from a liquid state to a solid state by reversible cycloaddition reactions within a time period of less than about 1 second.

3. The composition of claim 1, wherein the liquid state comprises a maleimide compound and a furan compound.

4. The composition of claim 3, wherein the maleimide compound is a bismaleimide and the furan compound is a bisfuran of the following structures:

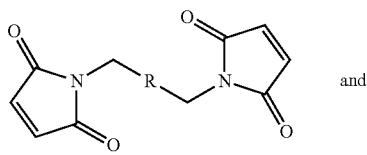

and

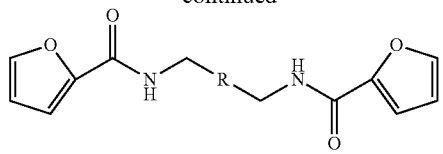

where each R, which can be the same or different, is a linking group.

5. The composition of claim 4, wherein R is selected from the group consisting of substituted or unsubstituted linear or branched alkyl groups, substituted or unsubstituted cyclic alkyl groups, substituted or unsubstituted aryl groups, substituted or unsubstituted arylalkyl groups, substituted or unsubstituted alkylaryl groups, and substituted or unsubstituted alkylenedioxy groups.

6. The composition of claim 4, wherein each R is the same.

7. The composition of claim 4, wherein R is selected from the group consisting of a C$_6$-alkyl group, a cyclohexyl group, a phenyl group, and a diethyleneoxy group.

8. The composition of claim 3, wherein the maleimide compound is a trigonal maleimide and the furan compound is a trigonal furan of the following structures:

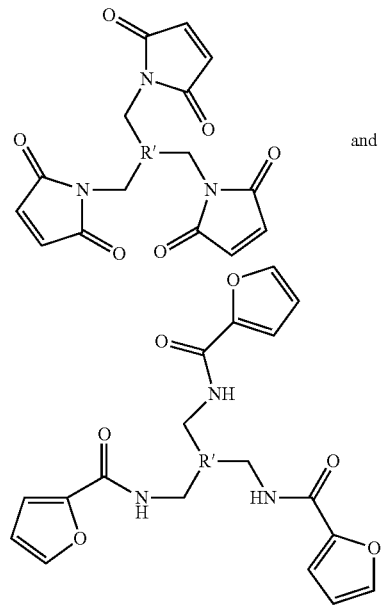

where each R', which can be the same or different, is a linking group.

9. The composition of claim 8, wherein R' is NR$_3$, and each R is selected from the group consisting of substituted or unsubstituted linear or branched alkyl groups, substituted or unsubstituted cyclic alkyl groups, substituted or unsubstituted aryl groups, substituted or unsubstituted arylalkyl groups, substituted or unsubstituted alkylaryl groups, and substituted or unsubstituted alkylenedioxy groups.

10. The composition of claim 9, wherein each R' is the same.

11. The composition of claim 9, wherein R is selected from the group consisting of a C$_6$-alkyl group, a cyclohexyl group, a phenyl group, and a diethyleneoxy group.

12. The composition of claim 3, comprising two or more different maleimide compounds and two or more different furan compounds.

13. The composition of claim 1, wherein the composition consists essentially of the reversible polymer material.

14. The composition of claim 1, wherein the composition consists essentially of the reversible polymer material and a radical scavenger as a stabilizer.

15. The composition of claim 1, wherein the composition has a viscosity of from about 1 to about 100 cPs at a temperature of from about 60 to about 140° C.

16. A composition, comprising a reversible polymer material, which can reversibly transition between a liquid state and a solid state by reversible cycloaddition reactions, wherein the composition has a viscosity of from about 2 to about 20 cPs at a temperature of from about 75 to about 120° C. and upon cooling, the reversible polymer material transitions from a liquid state to a solid state by reversible cycloaddition reactions within a time period of less than about 10 seconds.

17. The composition of claim 16, wherein the liquid state comprises at least a mixture of a maleimide compound and a furan compound.

18. A method of making a polymer film, comprising:
applying a composition comprising a reversible polymer material, which can reversibly transition between a liquid state and a solid state by reversible cycloaddition reactions, to a substrate in a liquid state; and
cooling the composition,
wherein upon cooling, the reversible polymer material transitions from a liquid state to a solid state by reversible cycloaddition reactions within a time period of less than about 10 seconds.

19. The method of claim 18, wherein the liquid state comprises at least a mixture of a bismaleimide compound and a bisfuran compound or a mixture of a trigonal maleimide compound and a trigonal furan compound.

20. The method of claim 18, wherein the composition has a viscosity of from about 2 to about 20 cPs at a temperature of from about 75 to about 120° C.

* * * * *